(12) United States Patent
Santjer

(10) Patent No.: US 8,131,381 B1
(45) Date of Patent: Mar. 6, 2012

(54) ELECTROTHERAPEUTIC DEVICE HAVING AN ELECTRODE ARRAY

(76) Inventor: Suzanne M. Santjer, Chesapeake, VA (US)

(*) Notice: Subject to any disclaimer, the term of this patent is extended or adjusted under 35 U.S.C. 154(b) by 269 days.

(21) Appl. No.: 12/384,018

(22) Filed: Mar. 31, 2009

Related U.S. Application Data

(60) Provisional application No. 61/072,510, filed on Mar. 31, 2008.

(51) Int. Cl.
*A61N 1/04* (2006.01)

(52) U.S. Cl. ......... 607/148; 607/145; 607/146; 607/150

(58) Field of Classification Search ........... 607/145–150
See application file for complete search history.

(56) References Cited

U.S. PATENT DOCUMENTS

| | | | |
|---|---|---|---|
| 3,827,403 A | 8/1974 | Meyer | |
| 4,153,009 A | 5/1979 | Boyle | |
| 4,685,466 A * | 8/1987 | Rau | 600/387 |
| 4,805,558 A | 2/1989 | Lehmann | |
| 5,109,848 A | 5/1992 | Thomas et al. | |
| 5,722,352 A | 3/1998 | Leatherman | |
| 6,171,239 B1 * | 1/2001 | Humphrey | 600/372 |
| 6,510,333 B1 * | 1/2003 | Licata et al. | 600/383 |
| 6,615,080 B1 | 9/2003 | Unsworth et al. | |
| 6,690,959 B2 | 2/2004 | Thompson | |
| 6,788,979 B1 | 9/2004 | Axelgaard et al. | |
| 7,331,964 B2 | 2/2008 | Maricle | |
| 2002/0035345 A1 * | 3/2002 | Beck | 604/20 |
| 2006/0064129 A1 | 3/2006 | Pujol | |
| 2008/0027507 A1 | 1/2008 | Bijelic et al. | |
| 2008/0208280 A1 | 8/2008 | Lindenthaler et al. | |
| 2008/0255649 A1 | 10/2008 | Herbert | |

\* cited by examiner

*Primary Examiner* — Scott Getzow
*Assistant Examiner* — Joseph Dietrich
(74) *Attorney, Agent, or Firm* — Wooten & Shaddock, PLC

(57) ABSTRACT

An electrotherapy device having an array of post electrodes that includes a body housing having a top surface; a plurality of apertures formed through the top surface of the body housing; a support member positioned within the body housing; and a plurality of post electrodes extending from the support member, through the apertures formed through the top surface of the body housing to form an array of post electrodes, wherein each of the post electrodes is formed of substantially rigid, electrically conductive material, wherein each post electrode terminates with a relatively blunt or rounded surface, and wherein each post electrode is electrically coupled to each other post electrode.

20 Claims, 4 Drawing Sheets

ELECTROTHERAPEUTIC DEVICE HAVING AN ELECTRODE ARRAY

CROSS-REFERENCE TO RELATED APPLICATIONS

This application claims the benefit of U.S. Provisional Application No. 61/072,510, filed Mar. 31, 2008, the disclosure of which is incorporated herein by reference.

BACKGROUND OF THE INVENTION

1. Field of the Invention

This invention relates generally to electrotherapeutic electrodes. In particular, the present invention relates to an electrotherapy device having an electrode array that provides improved skin contact through materials such as hair or fabric.

2. Description of Related Art

There are a wide variety of commercially available electrodes used to apply electrical physical therapy modalities to both humans and animals. The gel electrode, for example, is a self-adhesive electrode that is commonly used in connection with electrical physical therapy modalities.

While there are a variety of electrical therapies that can be employed, one of the most widely used electrical therapies is Microcurrent Electrical Therapy (MET), which is also know as Microcurrent Electrical Nerve Stimulation (MENS).

An Alpha-Stim is a microcurrent device that can be used to perform microcurrent therapy. Microcurrent therapy is a type of therapy that can be used, particularly on animals, because microcurrent therapy is low intensity (microamperes) and low frequency and does not produce an intense sensation. Such therapies can be used to control pain and induce healing by increasing circulation and cellular Adenosine Triphosphate (ATP) production.

SUMMARY OF THE INVENTION

Unfortunately, gel electrodes are not ideal for use where there is fur or hair, or in situations where it would be advantageous to apply electrical stimulation through fabric or other material. Typically, before electrical stimulation can be provided to a target area where there is fur or hair, the target area must first be shaved before a known electrode can be placed over the area. Otherwise, the fur or hair impedes contact between the electrode and the surface of the skin. Shaving a target area is not always practical or desired.

The electrotherapy device of the present invention provides an array of post electrodes that can be used in target areas that are covered by hair or fur without shaving the target area.

In various exemplary, nonlimiting embodiments, electrotherapy device comprises an array of post electrodes that extend from a body housing. Each of the post electrodes is an electrical conductor that is electrically coupled, via an electrical connector, to an iontophoretic dose controller.

Once coupled to the iontophoretic dose controller, current can be passed through each of the post electrodes such that each post electrode acts as a conductive interface between the patient's skin and a iontophoretic dose controller.

Unlike known electrodes, each of the post electrode in the electrode array extends from the body housing so as to be able to penetrate through fur, hair, or fabric. Thus, the electrotherapy device of the present invention can be used over fur or hair on animal or human patients. In various exemplary embodiments, a coupling gel or saline solution may be used on the skin to improve conduction of the electrical current.

Each of the post electrodes is comprised of a substantially rigid material, such that the post electrodes are capable of penetrating through fur, hair, or fabric without significant flexing. In this manner, the overall size and shape of the post electrode array is not altered when the post electrodes come in contact with either fur, hair, or fabric, or the skin of the patient.

The electrotherapy device can be used to stimulate as in the application of electrical physical therapy modalities or used as a recording electrode for the detection of ECG, EEG, and EMG signals. Additionally, the electrotherapy device can be used to provide other types of electrical therapies, including, but not limited to Transcutaneous Electrical Nerve Stimulation (TENS), High Volt Pulsed Galvanic (HVPG), and Interferential Stimulation (INF).

In certain exemplary embodiments, the electrotherapy device can also be used as a monitor to detect minute voltages (surface biopotentials) generated by the brain to activate muscles or nerves. The electrotherapy device can also be used in electrical bioimpedance studies.

Accordingly, this invention provides an electrical stimulation electrotherapy device having an electrode array that provides improved skin contact through materials such as hair or fabric.

This invention separately provides an electrotherapy device having an electrode array that can be utilized with an iontophoretic dose controller for administering iontophoretic treatments.

This invention separately provides an electrotherapy device having an electrode array having multiple posts that are able to penetrate through hair or fur to contact the skin..

These and other features and advantages of this invention are described in or are apparent from the following detailed description of the exemplary embodiments.

BRIEF DESCRIPTION OF THE DRAWINGS

The exemplary embodiments of this invention will be described in detail, with reference to the following figures, wherein like reference numerals refer to like parts throughout the several views, and wherein.

DETAILED DESCRIPTION OF EXEMPLARY EMBODIMENTS

For simplicity and clarification, the design factors and operating principles of the electrotherapy devices of this invention are explained with reference to various exemplary embodiments of an electrotherapy device having an electrode array according to this invention. The basic explanation of the design factors and operating principles of the electrotherapy device is applicable for the understanding, design, and operation of the electrotherapy device of this invention.

It should be appreciated that the terms "electrode", "array", and "electrode array" are used for basic explanation and understanding of the systems, methods, and/or apparatuses of this invention. Therefore, the terms "electrode", "array", and "electrode array" are not to be construed as limiting the systems, methods, and apparatuses of this invention.

It should also be understood that the absence of specific detail regarding the iontophoretic dose controller with which the electrotherapy device is utilized is intentional as the electrotherapy device is designed to be utilized with a wide variety and combination of existing iontophoretic dose controllers or other electrical therapy units.

Figure 1:
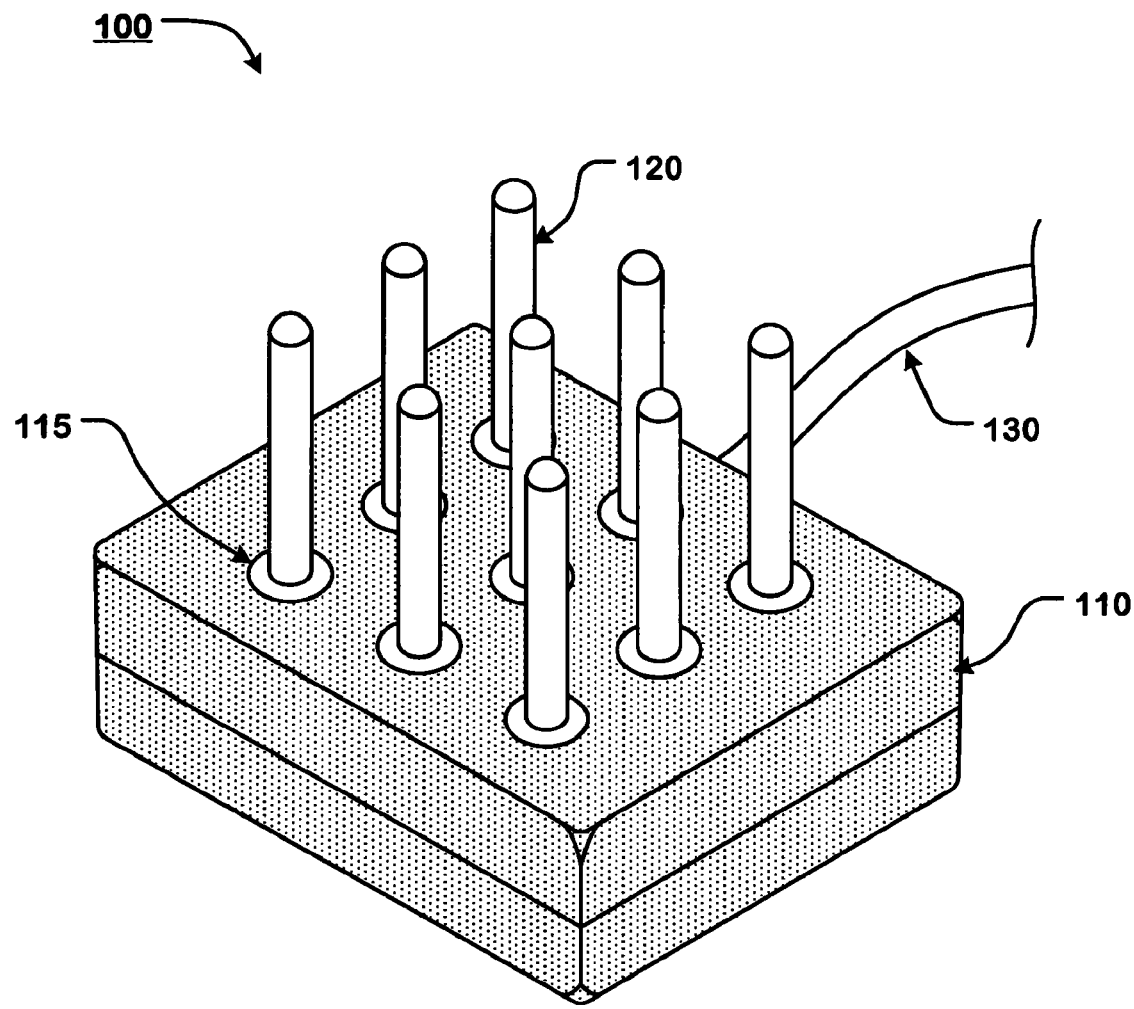
FIG. 1 shows a perspective view of a first exemplary embodiment of an electrotherapy device having an electrode array according to this invention.
Figure 2A:
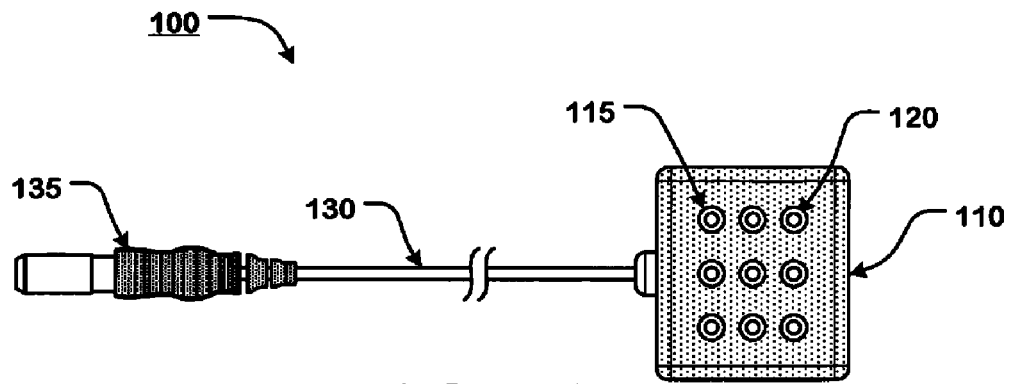
FIG. 2A shows a top view of the first exemplary embodiment of the electrotherapy device according to this invention.
Figure 2B:
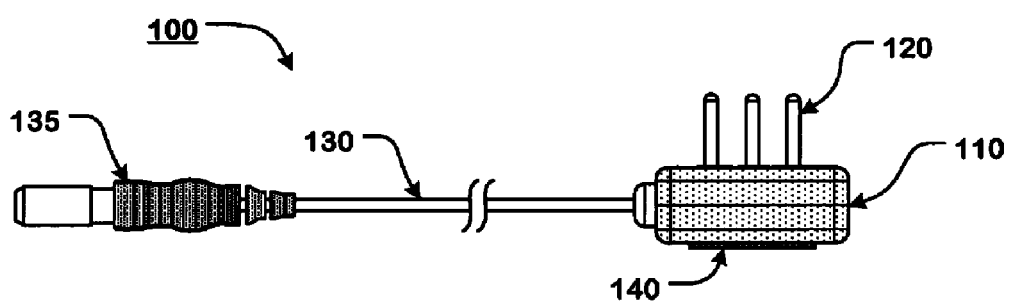
FIG. 2B shows a side view of the first exemplary embodiment of the electrotherapy device according to this invention.
Figure 2C:
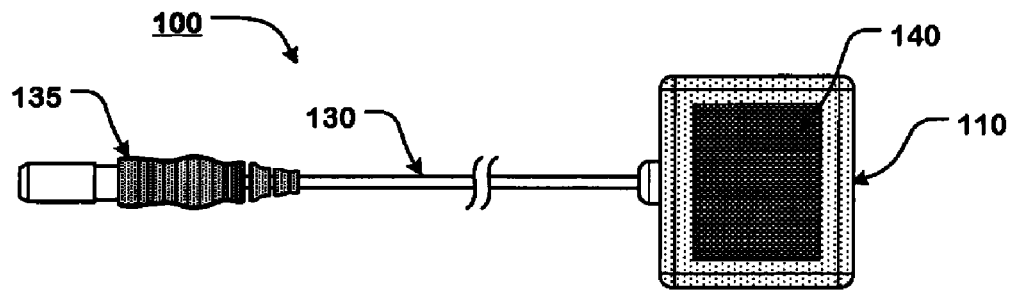
FIG. 2C shows a bottom view of the first exemplary embodiment of the electrotherapy device according to this invention.
Figure 2D:
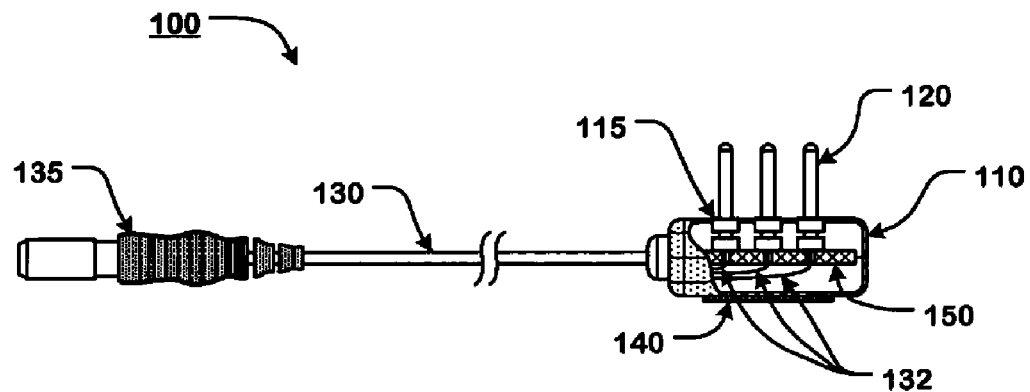
FIG. 2D shows a partial cut-away side view of the first exemplary embodiment of the electrotherapy device according to this invention.

Turning now to the drawing figures, FIGS. 1-2D illustrate various views of a first exemplary embodiment of an electrotherapy device, according to this invention. As shown in FIGS. 1-2D, the electrotherapy device 100 comprises at least some of a body housing 110 and a plurality of post electrodes 120.

In various exemplary embodiments, the body housing 110 comprises a non-conductive material and provides a housing for a support member 150. The body housing 110 includes a top surface. In various exemplary embodiments, the top surface of the body housing 110 is substantially plainer. Alternatively, the top surface of the body housing may be substantially concave or convex in at least one direction.

Figure 4:
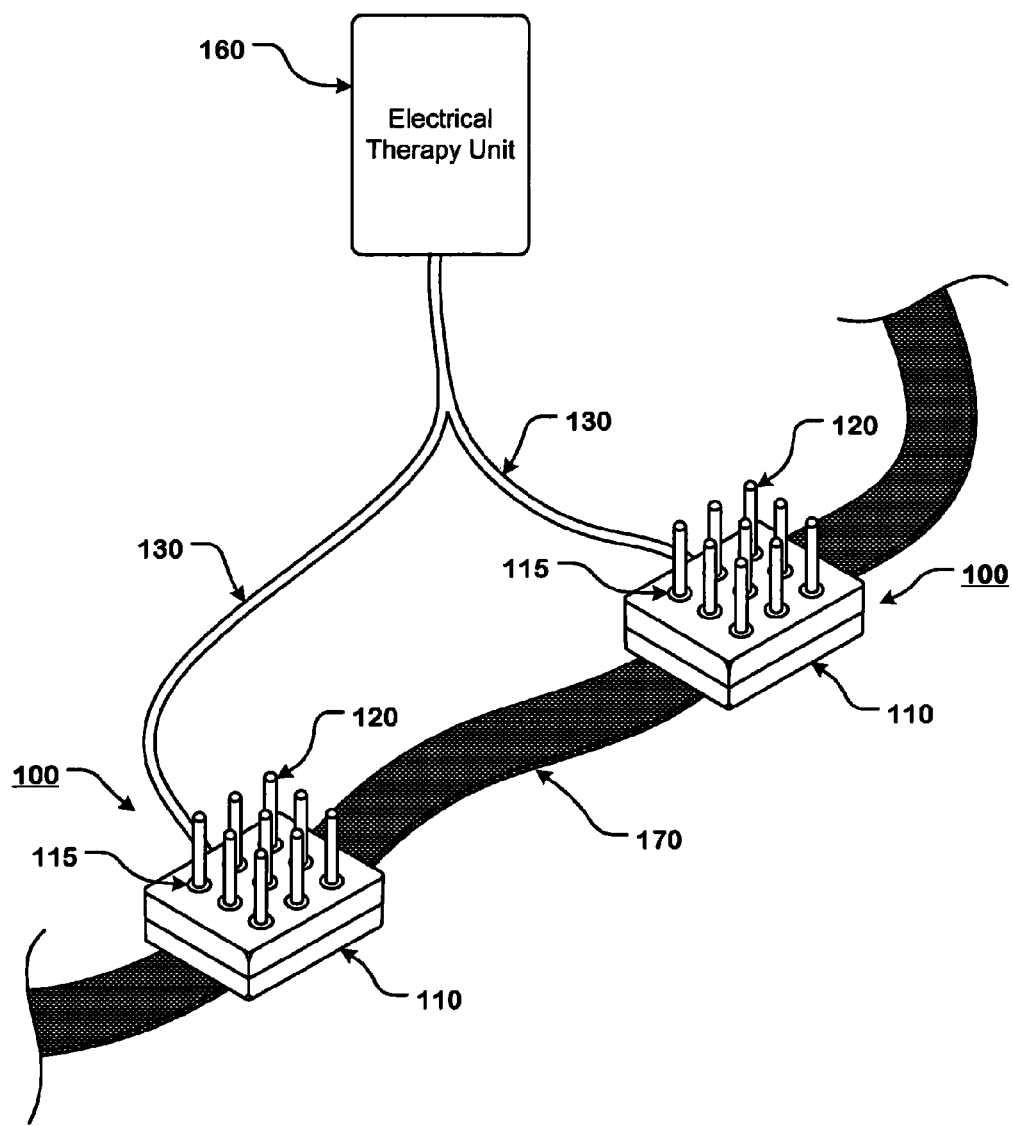
FIG. 4 shows an exemplary electrical stimulation assembly utilizing two of the electrotherapy devices according to this invention.

The body housing 110 includes a plurality of apertures 115 formed through the top surface, through which the post electrodes 120 extend. The body housing may also include a securing element 140 position so as to allow the body housing 110 to be permanently or removably attached or coupled to, for example, a strap element 170, as shown in FIG. 4. In various exemplary embodiments, the securing element 140 comprises a portion of Velcro or other hook-and-loop fastener material, a male/female snap-release buckle, button, rivet, snap, or other known or later developed fastening or securing means.

Each of the post electrodes 120 is formed of substantially rigid, electrically conductive material, such as, for example, a metal. The post electrodes 120 are secured to the support member 150 so as to extend through the apertures 115 of the body housing 110, when the support member 150 is positioned within the body housing 110. In various exemplary embodiments, the post electrodes 120 extend substantially perpendicular to a longitudinal axis of the body housing 110.

In certain exemplary embodiments, the support member 150 comprises a nonconductive material and each post electrode 120 is electrically coupled to the electrical connection 130 by a secondary electrical connection 132. It should be appreciated that the secondary electrical connection 132 may comprise circuitry etched or otherwise embedded in the support member 150. Alternatively, the support member 150 may comprise a conductive material that is electrically coupled to the electrical connection 130, such that each post electrode 120 is electrically coupled to the electrical connection 130, via its electrical connection to the support member 150.

In various exemplary embodiments, each post electrode 120 extends between approximately 0.1 to 0.6 inches above the top surface of the body housing 110. In other exemplary embodiments, each post electrode extends between approximately 0.1 to 0.4 inches above the top surface of the body housing 110. In still other exemplary embodiments, each post electrode extends approximately 0.2 inches above the top surface of the body housing 110. In various exemplary, non-limiting embodiments, the diameter of each post electrode 120 is approximately 0.06 inches.

Each post electrode 120 terminates with a sufficiently blunt, or rounded (as shown) surface. In this manner, each terminal end of each post electrode 120 is able to come into contact with the skin of the patient without puncturing or damaging the patient's skin.

In certain exemplary embodiments, each post electrode 120 includes a nonconductive sleeve that extends along at least a portion of the post electrode 120.

It should be appreciated that the overall size and shape of each post electrode 120 is a design choice based upon the desired functionality of the electrotherapy device 100.

Each of the post electrodes 120 is electrically coupled, via an electrical connection 130, to a electrical connector 135. In various exemplary embodiments, the electrical connection 130 comprises a plurality of electrical connections 132.

The electrical connector 135 allows the electrotherapy device 100 to be electrically coupled to an appropriate iontophoretic dose controller, such as, for example, the electrical therapy unit 160, as shown in FIG. 4.

It should be understood that while the array of post electrodes 120 is shown as including nine post electrodes 120 arranged in a relatively square pattern, the number and arrangement of post electrodes 120 is a design choice based upon the desired functionality and coverage area of the electrotherapy device 100. Thus, for example, the electrotherapy device 100 may comprise more or less than nine post electrodes 120, arranged in a substantially square, rectangular, circular, triangular, starburst, or other geometric or random pattern.

Figure 3:
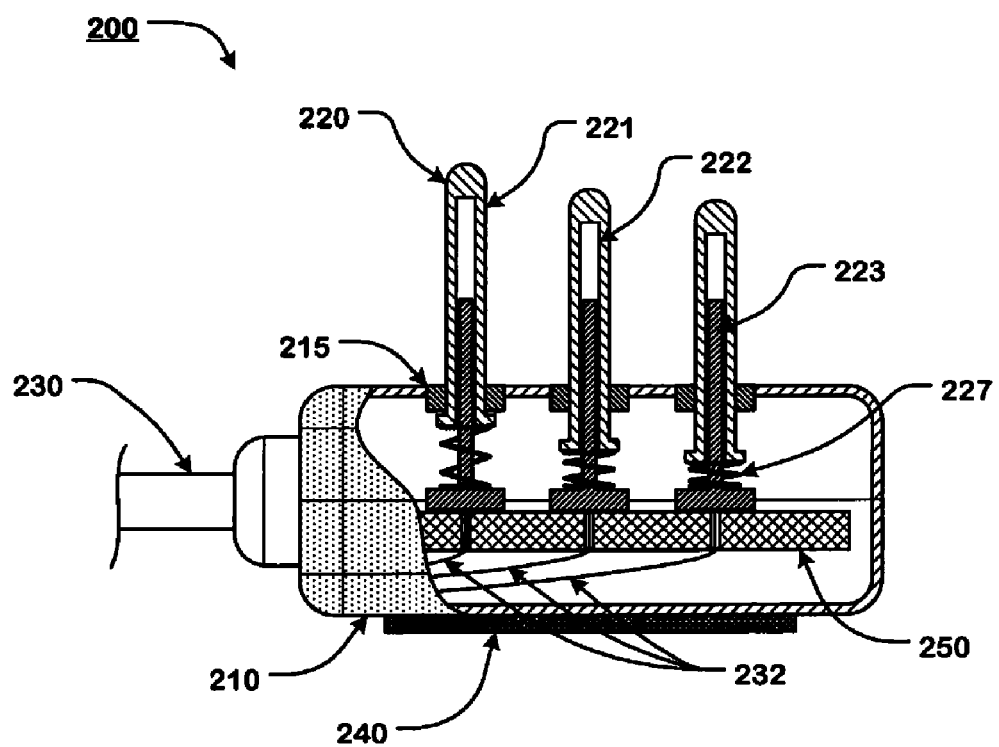
FIG. 3 shows a partial cut-away side view of a second exemplary embodiment of an electrotherapy device according to this invention.

FIG. 3 shows a partial cut-away side view of a second exemplary embodiment of an electrotherapy device according to this invention. As shown in FIG. 3, the electrotherapy device 200 comprises at least some of a body housing 210 having a plurality of apertures 215, an electrical connection 230 optional comprising a plurality of electrical connections 232, a electrical connector (not shown), an optional securing element 240, and a support member 250.

It should be understood that each of these elements, if included, corresponds to and operates similarly to the body housing 110 having a plurality of apertures 115, an electrical connection 130 optional comprising a plurality of electrical connections 132, a electrical connector (not shown), an optional securing element 140, and a support member 150, as described above with reference to the electrotherapy device 100 of FIGS. 1-2D.

However, as shown in FIG. 3, each of the plurality of post electrodes 220, while operating similarly to the post electrodes 120 described above, is spring biased so as to be at least partially retractable. As shown, each post electrode 220 comprises an electrode shell 221 that includes a cavity 222 formed therein. Each post electrode 220 further comprises an electrode post 223 that is coupled to the support member 250. Each electrode post 223 is formed so as to be received within the cavity 222 formed in a corresponding electrode shell 221. When each electrode shell 221 is positioned atop its respective electrode post 232, the electrode shell 221 is able to slide up and down its electrode post 232.

A spring biasing means 227, such as, for example, a coil spring, is positioned proximate a base of each electrode post 232 so as to engage and provide a spring biasing force to each electrode shell 221. In this manner, each electrode shell is spring biased to an extended position.

When the electrotherapy device 200 is utilized and a terminal end of a post electrode 220 comes in contact with a patient's skin, a spring biased of the spring biasing means 227 is overcome so as to allow the electrode shell 221 to slide down its electrode post 232. In this manner, it is more likely that each of the electrode posts 220 in the electrode post array is able to come into contact with the patient's skin, particularly if the electrotherapy device 200 is utilized in an area having an uneven surface.

FIG. 4 shows an exemplary electrical stimulation assembly utilizing two of the electrotherapy devices according to this invention. As illustrated, the two electrotherapy devices 100 are attached or coupled, via the securing element (not shown), to an exemplary strap element 170. Utilizing a strap element 170, the electrotherapy devices 100 can be attached to a body part of a patient. In various exemplary embodiments, at least a portion of the strap element 170 may include a flexible or elastic portion to allow for a measure of expansion of the strap element 170 so that the strap element 170 can expand to make the electrical stimulation assembly easier to apply to a patient or provide increased freedom of movement for the patient while the electrical stimulation assembly is being worn.

It should be appreciated that while the electrical stimulation assembly, as illustrated in FIG. 4, includes two electrotherapy devices 100 any number of electrotherapy devices 100 or 200 may be utilized to form the electrical stimulation assembly.

Each electrotherapy device 100 may be permanently or removably electrically coupled to the electrical therapy unit 160, such that signals from the electrical therapy unit 160 can be transmitted to the electrode posts 120.

While this invention has been described in conjunction with the exemplary embodiments outlined above, it is evident that many alternatives, modifications, and variations will be apparent to those skilled in the art. Any and all such adaptations, modifications, and variations should and are intended to be comprehended within the meaning and range of equivalents of the disclosed exemplary embodiments.

It is to be understood that the phraseology of terminology employed herein is for the purpose of description and not of limitation. Accordingly, the foregoing description of the exemplary embodiments of the invention, as set forth above, are intended to be illustrative, not limiting. Various changes, modifications, and/or adaptations may be made without departing from the spirit and scope of this invention.

What is claimed is:

1. An electrotherapy device having an array of post electrodes, comprising:
   a body housing having a top surface;
   a plurality of apertures formed through the top surface of the body housing;
   a support member positioned within the body housing; and
   a plurality of post electrodes extending from the support member, through the apertures formed through the top surface of the body housing to form an array of post electrodes, wherein each of the post electrodes is formed of substantially rigid, electrically conductive material, wherein each post electrode terminates with a relatively blunt or rounded surface, and wherein each post electrode is electrically coupled to each other post electrode, wherein each of the plurality of post electrodes is at least partially retractable.

2. The electrotherapy device of claim 1, wherein the body housing comprises a non-conductive material.

3. The electrotherapy device of claim 1, wherein the top surface of the body housing is substantially plainer in at least one direction.

4. The electrotherapy device of claim 1, wherein the top surface of the body housing is substantially concave in at least one direction.

5. The electrotherapy device of claim 1, wherein the top surface of the body housing is substantially convex in at least one direction.

6. The electrotherapy device of claim 1, wherein the body housing includes a securing element position so as to allow the body housing to be permanently or removably attached or coupled to a strap element.

7. The electrotherapy device of claim 1, wherein the support member comprises a nonconductive material and each post electrode is electrically coupled to an electrical connection by a secondary electrical connection.

8. The electrotherapy device of claim 7, wherein the secondary electrical connection comprised circuitry etched or otherwise embedded in the support member.

9. The electrotherapy device of claim 1, wherein the support member comprises an electrically conductive material that is electrically coupled to an electrical connection, such that each post electrode is electrically coupled to the electrical connection, via an electrical connection to the support member.

10. The electrotherapy device of claim 1, wherein the post electrodes extend substantially perpendicular to a longitudinal axis of the body housing.

11. The electrotherapy device of claim 1, wherein each post electrode extends between approximately 0.1 to 0.6 inches above the top surface of the body housing.

12. The electrotherapy device of claim 1, wherein each post electrode extends between approximately 0.1 to 0.4 inches above the top surface of the body housing.

13. The electrotherapy device of claim 1, wherein each post electrode extends approximately 0.2 inches above the top surface of the body housing.

14. The electrotherapy device of claim 1, wherein each post electrode includes a nonconductive sleeve that extends along at least a portion of the post electrode.

15. The electrotherapy device of claim 1, wherein a diameter of each post electrode is approximately 0.06 inches.

16. The electrotherapy device of claim 1, wherein each of the post electrodes is electrically coupled to an electrical connection that allows the electrotherapy device to be electrically coupled to an appropriate iontophoretic dose controller.

17. The electrotherapy device of claim 1, wherein the post electrodes are arranged in a substantially square, rectangular, circular, triangular, starburst, or other geometric or random pattern.

18. The electrotherapy device of claim 1, wherein each of the plurality of post electrodes at least partially retractable relative to the top surface of the body housing.

19. The electrotherapy device of claim 1, wherein each of the plurality of post electrodes is spring biased to an extended position.

20. The electrotherapy device of claim 1, wherein at least two electrotherapy devices are attached or coupled, via a securing element, to a strap element to form a electrical stimulation assembly.

\* \* \* \* \*